United States Patent
Amit et al.

(10) Patent No.: US 8,923,949 B2
(45) Date of Patent: Dec. 30, 2014

(54) TRANSESOPHAGEAL ECHOCARDIOGRAPHY CAPSULE

(75) Inventors: Mati Amit, Zur-Yigal (IL); Meir Bar-Tal, Haifa (IL); Yitzhack Schwartz, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 21 days.

(21) Appl. No.: 13/158,897

(22) Filed: Jun. 13, 2011

(65) Prior Publication Data
US 2012/0150024 A1   Jun. 14, 2012

Related U.S. Application Data

(60) Provisional application No. 61/357,703, filed on Jun. 23, 2010.

(51) Int. Cl.
| A61B 5/05 | (2006.01) |
|---|---|
| A61B 8/12 | (2006.01) |
| A61B 8/00 | (2006.01) |
| A61B 1/00 | (2006.01) |
| A61B 1/04 | (2006.01) |
| A61B 1/273 | (2006.01) |

(52) U.S. Cl.
CPC ........... *A61B 1/00082* (2013.01); *A61B 8/4472* (2013.01); *A61B 1/00154* (2013.01); *A61B 1/041* (2013.01); *A61B 8/12* (2013.01); *A61B 1/00158* (2013.01); *A61B 1/00101* (2013.01); *A61B 1/00128* (2013.01); *A61B 1/2733* (2013.01)
USPC ............................ 600/424; 600/443; 600/459

(58) Field of Classification Search
USPC ......... 600/101, 107, 175, 424, 437, 443, 463, 600/459, 447, 476
See application file for complete search history.

(56) References Cited

U.S. PATENT DOCUMENTS

| 5,634,466 A | 6/1997 | Gruner |
|---|---|---|
| 6,332,089 B1 | 12/2001 | Acker et al. |
| 7,860,578 B2* | 12/2010 | Jung et al. ..................... 607/122 |
| 7,918,786 B2* | 4/2011 | Kawano et al. ............... 600/117 |
| 2002/0077529 A1 | 6/2002 | Zotz |
| 2003/0028107 A1 | 2/2003 | Miller et al. |
| 2004/0133076 A1 | 7/2004 | Kobayashi et al. |
| 2005/0187479 A1* | 8/2005 | Graumann ..................... 600/476 |
| 2007/0083121 A1 | 4/2007 | Hastings et al. |
| 2007/0276226 A1 | 11/2007 | Tal |
| 2009/0076395 A1* | 3/2009 | Cespedes ....................... 600/462 |
| 2009/0270736 A1* | 10/2009 | Miyamoto et al. ............. 600/462 |

FOREIGN PATENT DOCUMENTS

| WO | WO 2009/022343 A2 | 2/2009 |
|---|---|---|
| WO | WO 2009/060460 A2 | 5/2009 |

OTHER PUBLICATIONS

Partial European Search Report dated Oct. 6, 2011 from related European Application No. 11171056.2.
Extended European Search Report dated Jan. 17, 2013 from related European Application No. 12182268.8.

* cited by examiner

*Primary Examiner* — Michael Rozanski (57) ABSTRACT

An imaging system, including a capsule, configured to enter an esophagus of a patient, having an ultrasonic transducer configured to image tissue of the patient. The system further includes an applicator tube configured to enter the esophagus, the tube being attachable to the capsule for positioning the capsule within the esophagus, and being detachable from the capsule after positioning of the capsule so as to permit the tube to be withdrawn from the esophagus while the capsule remains in position in the esophagus.

21 Claims, 8 Drawing Sheets

TRANSESOPHAGEAL ECHOCARDIOGRAPHY CAPSULE

CROSS-REFERENCE TO RELATED APPLICATION

This application claims the benefit of U.S. Provisional Patent Application 61/357,703, filed 23 Jun. 2010, which is incorporated herein by reference.

FIELD OF THE INVENTION

The present invention relates generally to imaging, and specifically to ultrasonic imaging via the esophagus of a patient.

BACKGROUND OF THE INVENTION

Transesophageal imaging systems are known in the art. Such systems typically require entry of a relatively thick tube into the esophagus of a patient being imaged. Entry of the tube typically causes discomfort to the patient, even though the patient of necessity has been sedated. Furthermore, an operator of the system typically needs to manipulate the system in the esophagus using the tube, generating further discomfort.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides an imaging system, including:

a capsule, configured to enter an esophagus of a patient, having an ultrasonic transducer configured to image tissue of the patient; and an applicator tube configured to enter the esophagus, the tube being attachable to the capsule for positioning the capsule within the esophagus, and being detachable from the capsule after positioning of the capsule so as to permit the tube to be withdrawn from the esophagus while the capsule remains in position in the esophagus.

Typically, the applicator tube includes a locking mechanism, and the capsule includes a retaining mechanism which mates with the locking mechanism, the locking mechanism and the retaining mechanism being operable so as to attach the tube to the capsule and detach the tube from the capsule.

In some embodiments the system includes a cable traversing a cavity of the applicator tube and coupled to the capsule, the cable being configured to transfer signals to and from the capsule. Typically, the signals include imaging signals generated by the ultrasonic transducer.

In a disclosed embodiment the capsule includes one or more microelectronic mechanical systems (MEMs), which are configured to position the ultrasonic transducer so that ultrasound from the transducer is directed towards the tissue of the patient.

In a further disclosed embodiment the capsule includes a balloon which is inflatable with a fluid, so that on inflation the balloon fixes the capsule to the esophagus. Typically the system includes tubing connected to the capsule via a cavity of the applicator tube, the tubing being configured to deliver the fluid to the balloon. In one embodiment the balloon has one or more electrodes. In an alternative embodiment a position of the transducer is adjusted in response to the inflation of the balloon.

Typically the capsule includes a capsule locator, configured to provide at least one of a location and an orientation of the capsule. The capsule locator may be a magnetic locating device.

In a yet further disclosed embodiment, the applicator tube includes a tube locator, configured to provide at least one of a location and an orientation of a distal end of the applicator tube.

The capsule may be cylindrical. In some embodiments the cylindrical capsule has a helical characteristic.

There is also provided, according to an embodiment of the present invention, a method for imaging, including:

inserting a capsule into an esophagus of a patient, the capsule having an ultrasonic transducer configured to image tissue of the patient; and inserting an applicator tube into the esophagus, the tube being attachable to the capsule for positioning the capsule within the esophagus, and being detachable from the capsule after positioning of the capsule so as to permit the tube to be withdrawn from the esophagus while the capsule remains in position in the esophagus.

There is also provided, according to an embodiment of the present invention, an imaging system, including:

a capsule, configured to enter an esophagus of a patient, having an ultrasonic transducer configured to image tissue of the patient;

a capsule locator, fixedly connected to the capsule, consisting of a first magnetic locating device providing a first signal, indicative of a first position of the capsule, in response to a magnetic field generated in a vicinity of the patient;

an applicator tube configured to enter the esophagus, the tube being attachable to the capsule for positioning the capsule within the esophagus, and being detachable from the capsule after positioning of the capsule so as to permit the tube to be withdrawn from the esophagus while the capsule remains in position in the esophagus; and a probe including a second magnetic locating device providing a second signal, indicative of a second position of the probe in the patient and registered with the first position, in response to the magnetic field.

There is also provided, according to an embodiment of the present invention, a method for imaging, including:

inserting a capsule into an esophagus of a patient, the capsule having an ultrasonic transducer configured to image tissue of the patient; and fixedly connecting a capsule locator to the capsule, the locator consisting of a first magnetic locating device providing a first signal, indicative of a first position of the capsule, in response to a magnetic field generated in a vicinity of the patient;

inserting an applicator tube into the esophagus, the tube being attachable to the capsule for positioning the capsule within the esophagus, and being detachable from the capsule after positioning of the capsule so as to permit the tube to be withdrawn from the esophagus while the capsule remains in position in the esophagus; and inserting into the patient a probe comprising a second magnetic locating device providing a second signal, indicative of a second position of the probe in the patient and registered with the first position, in response to the magnetic field.

The present disclosure will be more fully understood from the following detailed description of the embodiments thereof, taken together with the drawings, in which:

DETAILED DESCRIPTION OF EMBODIMENTS

Overview

An embodiment of the present invention provides a transesophageal ultrasound imaging system, which may typically be used to provide ultrasound images of heart tissue of a patient. The system comprises an imaging capsule having an ultrasonic transducer, and the capsule is sized so as to be able to enter the esophagus of the patient. Typically, the transducer is mounted on one or more microelectronic mechanical system (MEMS) pistons, which allow the transducer to be translated and/or oriented while the capsule is fixed in the esophagus. The capsule itself may also include a MEMS rotation device allowing the whole capsule to be reoriented in the esophagus.

The system also comprises an applicator tube which is also sized to enter the patient's esophagus. The capsule and tube comprise locking and retaining mechanisms which enable the tube and capsule to be attached for positioning the capsule in the esophagus. Once the capsule is in a desired position in the esophagus, the mechanisms may be activated to detach the tube from the capsule. This detachment enables the tube to be withdrawn from the esophagus, while the capsule remains in position in the esophagus.

Typically, image and control signals to and from the capsule, as well as power to the capsule, may be provided via a thin cable connected to the capsule. The cable is typically threaded through a cavity of the applicator tube.

After withdrawal of the applicator tube from the esophagus, only the capsule and its thin connecting cable remain in the patient, considerable enhancing the patient's comfort compared to prior art transesophageal imaging systems. The enhanced patient comfort means that longer and more thorough imaging, typically using the MEMS devices referred to above, may be performed on the patient.

System Description

Figure 1:
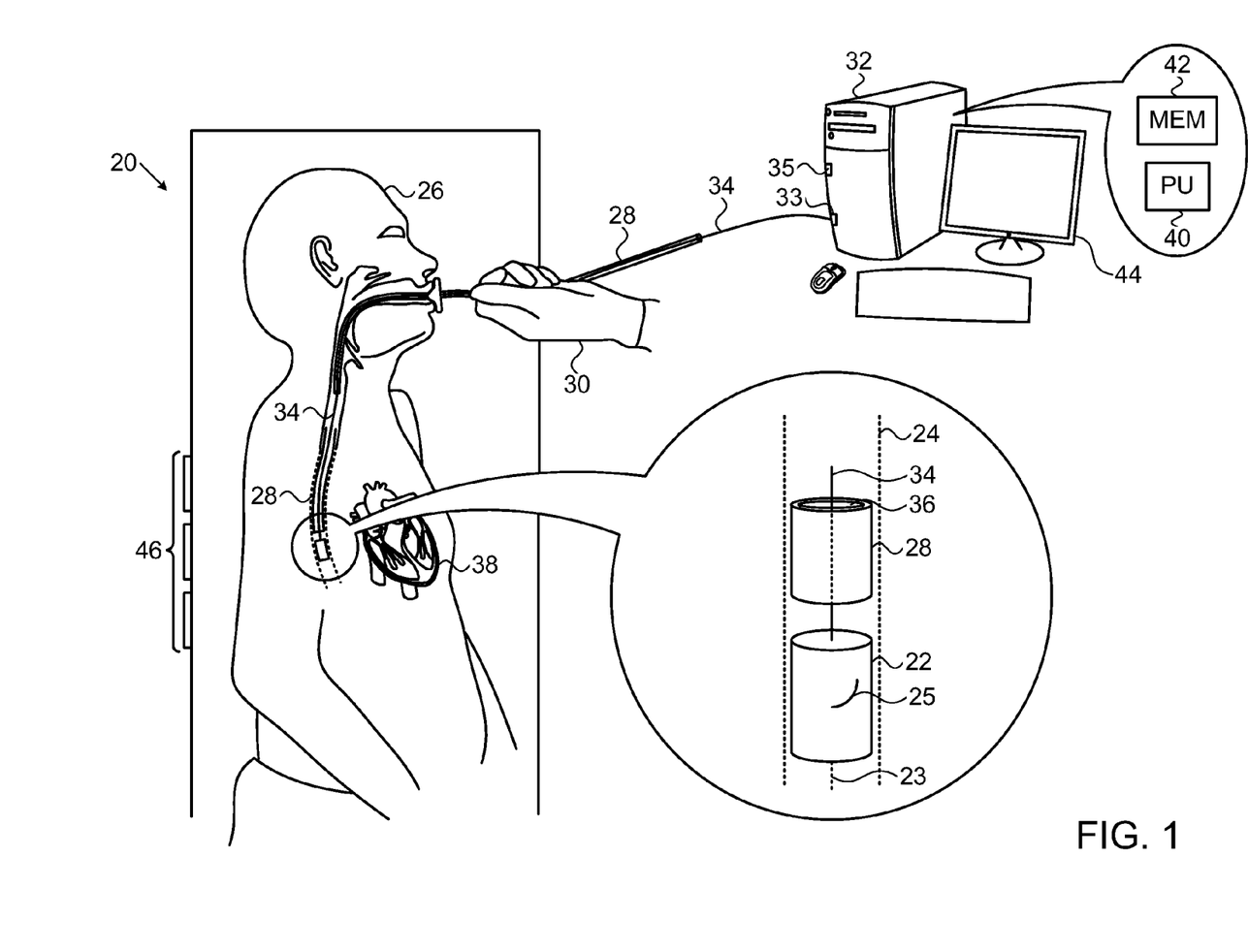
FIG. 1 is a schematic diagram of an imaging system, according to an embodiment of the present invention.

Reference is now made to FIG. 1, which is a schematic diagram of an imaging system 20, according to an embodiment of the present invention. System 20 comprises an imaging capsule 22, which is sized so that it is able to enter and be positioned in an esophagus 24 of a patient 26. Typically, capsule 22 is cylindrical having a central axis 23. In some embodiments, capsule 22 may be generally cylindrical with a helical characteristic, such as by having a helix or a partial helix 25 formed in the outer surface of the capsule.

System 20 also comprises an applicator tube 28, which is also sized so as to be able to enter the esophagus of the patient. Tube 28 is able to attach to and detach from capsule 22. Consequently, when the tube and the capsule are attached, an operator 30 of the system is able to use his or her hand to push or pull on the tube, and so move the capsule to a desired location within esophagus 24. When tube 28 and capsule 22 are detached, the operator is able to withdraw the tube from esophagus 24, leaving the imaging capsule remaining in position at the desired location.

Capsule 22 is coupled to a system controller 32 by a thin cable 34, which allows the controller to power the capsule. The cable also enables the controller to transmit and receive operational signals to and from the capsule, as well as to receive image signals from the capsule. Typically, cable 34 is a small diameter coaxial cable. A multiplexer 33 in controller 32 is connected to cable 34, and the cable connects between the multiplexer and the capsule by being placed within a central cavity 36 of applicator tube 28. The function of multiplexer 33 is explained below. In some embodiments, at least some of the operational and image signals are transmitted wirelessly between the controller and the capsule.

In some embodiments controller 32 comprises a fluid supply 35 (for clarity, tubing coupled to the supply is not shown in FIG. 1). Supply 35 is typically a closed loop supply, and comprises a heat exchanger allowing cooling of the fluid. The function of supply 35 is described below.

In the description herein operator 30 is assumed to use capsule 22 during a procedure for imaging tissue of a heart 38 of patient 26. However, it will be understood that such a procedure is described by way of example, and that operator 30 may position capsule 22 within esophagus 24 to image substantially any other tissue of the patient in proximity to the esophagus.

System controller 32 comprises a processing unit 40 communicating with a memory 42. The controller, under overall control of operator 30, uses software stored in memory 42 for processing the signals from the capsule, as well as to perform other functions related to the operation of system 20. Results of the operations performed by controller 32 are presented to the operator on a screen 44, which typically displays a graphic user interface to the operator, and/or an image of heart 38. The software may be downloaded to controller 32 in electronic form, over a network, for example, or it may, alternatively or additionally, be provided and/or stored on non-transitory tangible media, such as magnetic, optical, or electronic memory.

During the imaging tissue procedure, controller 32 may track capsule 22 and tube 28 using signals from magnetic locating devices, such as are used in the CARTO® navigation system produced by Biosense Webster, of Diamond Bar, Calif. incorporated into the capsule and the tube. The magnetic locating devices (described in more detail below), typically one or more coils, provide their signals to the controller in response to a magnetic field transmitted by magnetic transmitters 46 located near patient 26. Alternatively or additionally, capsule 22 and tube 28 may be tracked by any other convenient tracking system known in the art. An example of such a tracking system is described below.

While the heart imaging procedure referred to above is typically performed with patient 26 lying horizontally, in the following description, for clarity, patient 26 is assumed to be oriented so that esophagus 24 is approximately vertical, such as may be the case for an electrophysiological procedure.

Figure 2:
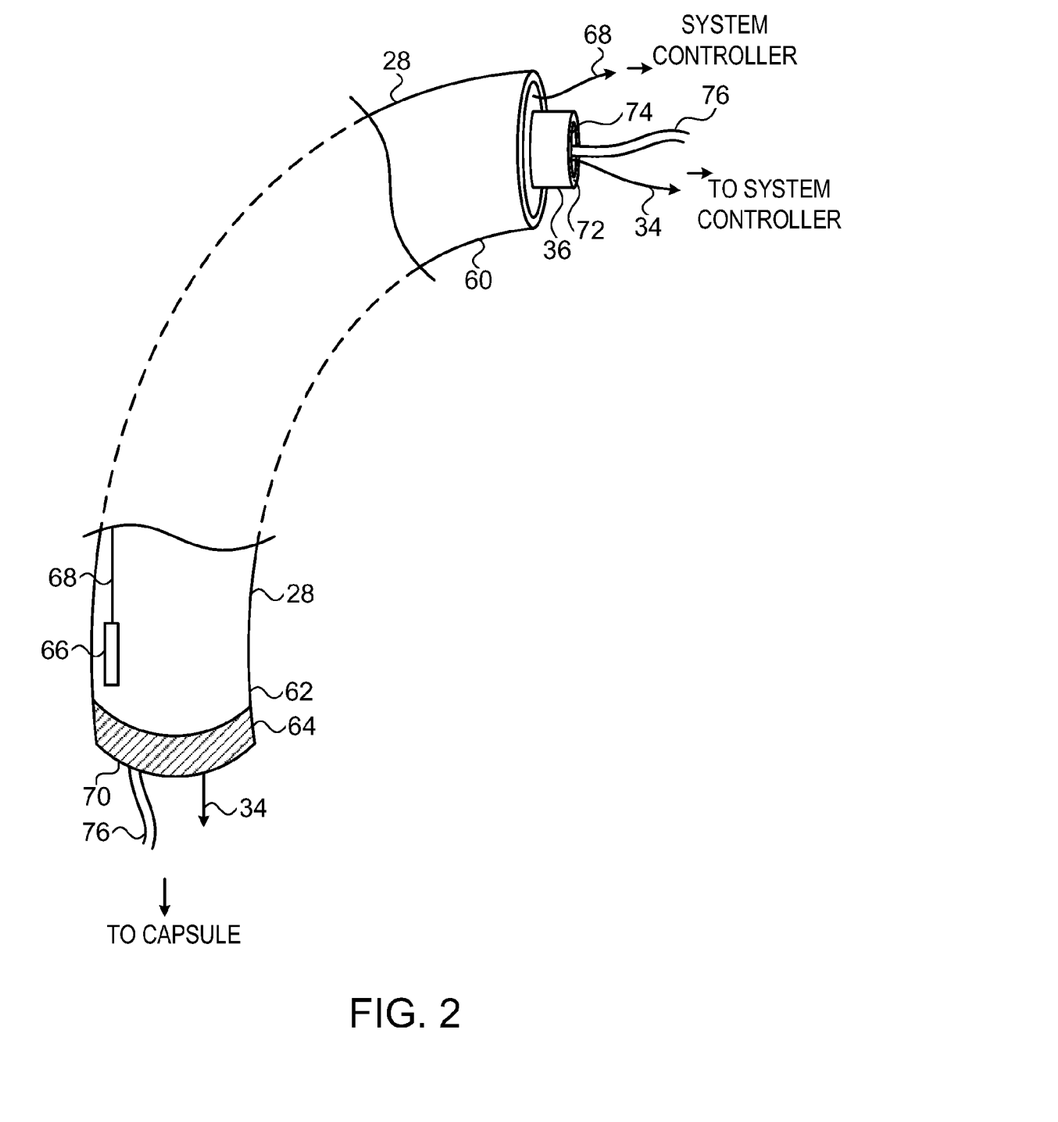
FIG. 2 is a schematic diagram of an applicator tube of the system, according to an embodiment of the present invention.

FIG. 2 is a schematic diagram of applicator tube 28, according to an embodiment of the present invention. The figure shows a proximal end 60 and a distal end 62 of the tube. Tube 28 is typically flexible, but has sufficient rigidity so as to be insertable into esophagus 24. In some embodiments tube 28 is constructed from material having variable elasticity, so that after insertion into the esophagus in a flexible, relatively rigid state, the elasticity may be changed so that the tube becomes flaccid.

An applicator tube locking mechanism 64 is implemented at the distal end of the tube. A tube distal end locator 66, typically a magnetic locating device, may be fixed to distal end 62. Locator 66 provides signals via a cable 68, in tube 28, to controller 32, so that the controller can track the location of the distal end. Applicator tube locking mechanism 64 mates with a capsule retaining mechanism of capsule 28. Both the tube locking mechanism and the capsule retaining mechanism are described in more detail below.

Locking mechanism 64 is activated by operator 30 using a locking activator 70. Herein, by way of example, activator 70 is assumed to be mechanical, comprising a locking tube 72 which traverses cavity 36, from proximal end 60 through to distal end 62, the distal end of tube 72 acting as the activator. Operator 30 activates the locking mechanism by pushing or pulling on the proximal end of locking tube 72. Other forms of locking mechanisms and activators will be apparent to those having ordinary skill in the art, including electromechanical and magnetic locking mechanisms and activators, and the scope of the present invention includes these forms.

Within tube 72 there is a further cavity 74, allowing passage of cable 34 between the proximal and distal ends of applicator tube 28. In some embodiments, thin tubing 76 also traverses cavity 74. Tubing 76 may be connected to fluid supply 35, and typically comprises a pair of tubes so that it may be used for transferring fluid to and from capsule 22 in a closed loop. The fluid is typically saline solution, and may be cooled by a heat exchanger in supply 35. As shown in the diagram, at proximal end 60 cable 68, tubing 76, and cable 34 are coupled to the system controller, and at distal end 62 tubing 76 and cable 34 are coupled to capsule 22.

Figure 3:
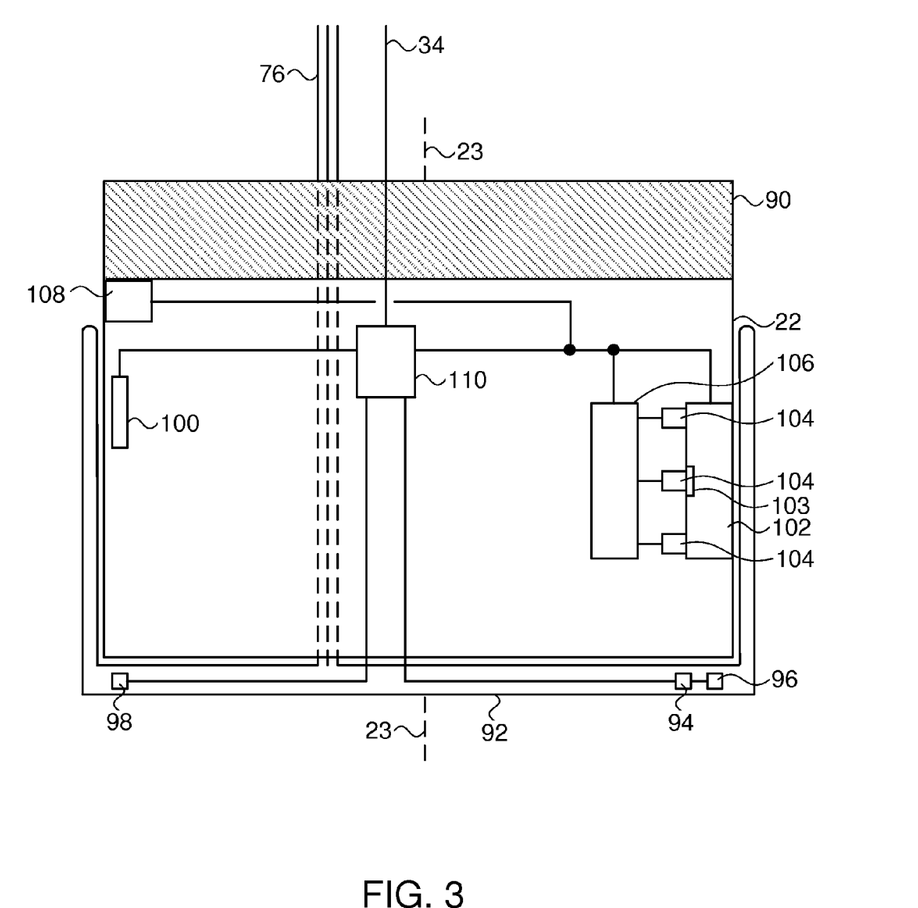
FIG. 3 is a schematic diagram of a capsule of the system, according to an embodiment of the present invention.

FIG. 3 is a schematic diagram of capsule 22, according to an embodiment of the present invention. Capsule 22 comprises on its upper surface a capsule retaining mechanism 90, which typically mechanically mates with applicator tube locking mechanism 64. In alternative embodiments, retaining mechanism 90 may comprise electromechanical and/or magnetic components, selected to mate with the alternative embodiments of the tube locking mechanism described above.

An inflatable balloon 92 may be coupled to the capsule and connected to tubing 76. Balloon 92 is typically implemented to at least partially surround the capsule. In some embodiments, the balloon is implemented so that when inflated, capsule 22 is located asymmetrically within the balloon, and so is located asymmetrically with respect to the esophagus. Such asymmetric location provides an ability for system 20 to adjust the location of capsule 22 with respect to tissue being imaged by the capsule. The balloon is configured so that when inflated, it exerts pressure against esophagus 24 so as to maintain capsule 22 in a fixed location with respect to the esophagus. Typically, a pressure sensor 94 and a temperature sensor 96 are attached to the balloon, so as to measure the pressure exerted by the balloon on the esophagus, as well as the temperature of the esophagus. In addition, in some embodiments, one or more electrodes 98 are attached to the balloon, and are configured to record esophageal and/or defibrillation signals.

Capsule 22 typically comprises a capsule locator 100, which may be generally similar to tube distal end locator 66. Capsule locator 100 provides controller 32 with location and/or orientation signals for tracking the position of the capsule. Electrodes 98 may also be configured to act as tracking or locating devices for the balloon and its coupled capsule, by measuring impedances from electrodes 98 to electrodes positioned on the skin of patient 26. In some embodiments at least some electrodes 98 may be located on capsule 22, rather than on the balloon.

Capsule 22 comprises an ultrasonic transducer 102, which is mounted within the capsule so as to transmit ultrasonic waves from the capsule. Transducer 102 also receives ultrasonic waves reflected from tissue such as heart 38. From signals generated by circuitry, typically analog electronic circuitry, in a transceiver 103 coupled to the transducer, and in response to the reflected waves, controller 32 is able to generate an image of the tissue, such as the heart, reflecting the waves.

Transducer 102 typically operates by transmitting its ultrasonic waves in a relatively narrow swathe, so typically imaging a slice of an organ such as the heart. In order to generate a complete image of the heart, the swathe transmitted needs to be scanned across the whole heart, and the images from each scan joined together to form the complete image. Embodiments of the present invention enable operator 30 to reorient transducer 102, by mounting the transducer on one or more microelectronic mechanical system (MEMS) based pistons 104, which are controlled by controller 32, typically via a MEMS driver 106. Such reorientation allows the operator to scan and image whole organs by only moving the transducer, without having to move capsule 22, so minimizing discomfort to patient 26.

In some embodiments, capsule 22 comprises a MEMS rotation engine 108, which is typically cylindrical in shape, and which, in response to signals from controller 32, rotates. Engine 108 is mounted at the edge of the capsule so that, in a deflated state of balloon 92, a surface of the engine contacts esophagus 24. Rotation of engine 108, while its surface contacts the esophagus, causes rotation of capsule 22 about axis 23. If capsule 22 is configured to have a helical characteristic, then rotation of engine 108 also causes the capsule to move vertically in the esophagus.

Control signals to the elements of capsule 22, and signals from the elements, may be transferred to and from the elements via a multiplexer 110. Multiplexer 110, together with multiplexer 33 in controller 32, allows signals to be transferred in a multiplexed format between the different elements of the capsule and the controller. Typically the signals of the different elements are transferred in a digitized serial format, so that cable 34, as a coaxial cable, is suitable for the transfer.

Figure 4A:
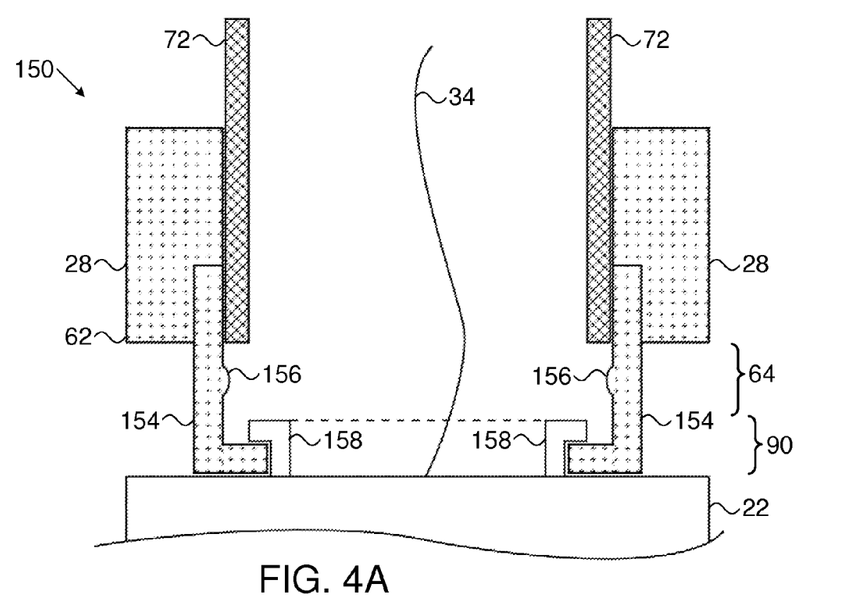
FIGS. 4A and 4B are schematic diagrams illustrating locking and retaining mechanisms, according to an embodiment of the present invention.
Figure 4B:
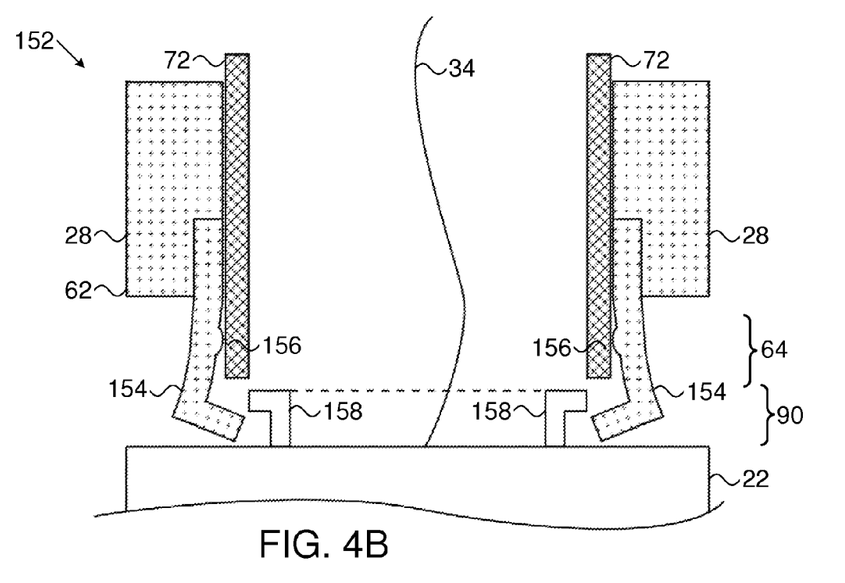

FIGS. 4A and 4B are schematic diagrams illustrating locking mechanism 64 and capsule retaining mechanism 90, according to an embodiment of the present invention. A first diagram 150 shows components of the mechanisms when capsule 22 is attached to tube 28. A second diagram 152 shows the components when the capsule is detached from the applicator tube.

Locking mechanism 64 comprises a plurality, typically three or more, of L-shaped elements 154, which are fixed to distal end 62 of the applicator tube. Each L-shaped element has a protrusion 156 projecting from the vertical leg of the element.

Retaining mechanism 90 comprises a circular ring element 158, which in cross-section has the form of an inverted-L and its mirror image.

As shown in diagram 150, in the attached state of the capsule and the applicator tube, tube 72 has moved in a proximal direction so that L-shaped elements 154 engage with ring element 158, and so that the tube does not contact protrusions 156. As shown in diagram 152, to attain the detached state of the capsule and tube, locking tube 72 is moved down in a distal direction to contact protrusions 156. The L-shaped elements are thus forced outwards, so disengaging with the ring element. The disengagement of the L-shaped elements with the ring element decouples or detaches the capsule from the applicator tube.

Figure 5:
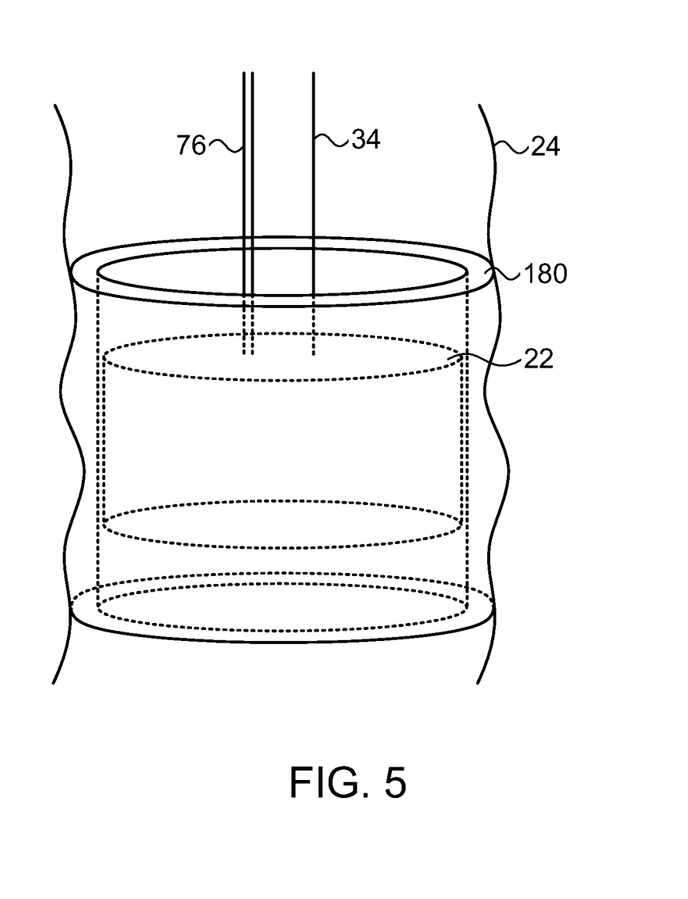
FIG. 5 is a schematic diagram of a retaining tube for the capsule of FIG. 3, according to an embodiment of the present invention.

FIG. 5 is a schematic diagram of a retaining tube for capsule 22, according to an embodiment of the present invention. In some embodiments of the present invention, rather than capsule 22 contacting esophagus 24, a retaining tube 180 is first placed in the esophagus. The retaining tube may be placed in the esophagus using an applicator tube similar to applicator tube 28. Once in position, capsule 22 may be positioned in the retaining tube using applicator tube 28. Using retaining tube 180 may facilitate movement of capsule 22 by operation of rotation engine 108, since the engine contacts the tube rather than the esophagus. In some embodiments retaining tube 180 is dissolvable in the esophagus, so that there is no requirement to withdraw the tube after it has been used in a procedure.

Figure 6:
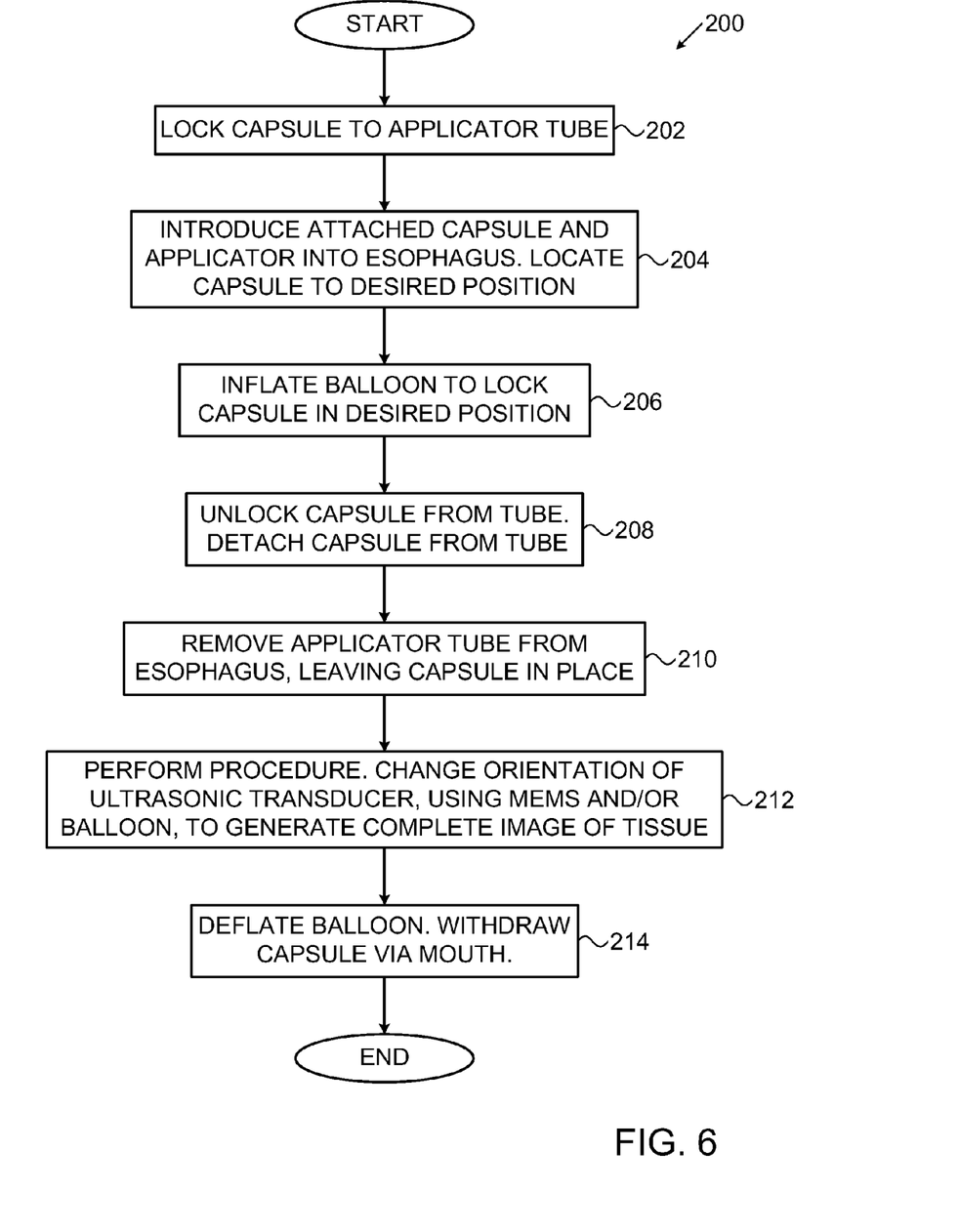
FIG. 6 is a flowchart describing steps performed during use of the system, according to an embodiment of the present invention.

FIG. 6 is a flowchart 200 describing steps performed during use of system 20, according to an embodiment of the present invention. The description assumes an embodiment having tubing 76, and that the tubing supplies saline solution fluid to balloon 92. The description also assumes that locators 66, 100 are operative in tube 28 and capsule 22. Those having ordinary skill in the art will be able to adapt the description for other embodiments described herein.

In a first step 202, capsule 22 and tube 28 are attached together using their locking and retaining mechanisms, as shown in diagram 150. Before the attachment, cable 34 and tubing 76 may be threaded from the capsule through cavity 74. The cable and tubing are then respectively connected to multiplexer 33 and fluid supply 35 in controller 32. To maintain the capsule and applicator tube in an attached state, the operator ensures that locking tube 72 does not touch protuberances 156, i.e., tube 72 is moved in a proximal direction.

In an initiate procedure step 204, operator 30 introduces the attached capsule and application tube into the esophagus of patient 26. Typically, the patient is mildly anesthetized before the introduction. Operator locates capsule 22 in a desired position in the esophagus using screen 44, which presents the position of the capsule using locators 100 and/or 66. The desired position for the capsule is in proximity to the tissue to be imaged, herein assumed to be heart 38, so that transceiver 103 is able to image the tissue. Alternatively or additionally, the operator may activate transceiver 103, and position the capsule using images generated by the transceiver.

In a fixation step 206, once capsule 22 is in its desired position, the operator inflates balloon 92 using fluid from fluid supply 35. Typically, after inflation, screen 44 presents temperature and pressure measurements of the esophagus, as registered sensors 94 and 96. Operator 30 may use the temperature and pressure values to ensure patient comfort. Alternatively or additionally, controller 32 may use the values to automatically adjust the level of inflation, and/or to provide a warning to the operator in case of an apparent problem, such as overheating of the esophagus. In some embodiments, fluid supply 35 circulates the fluid to balloon 92, enabling improved control of the temperature and pressure.

Typically, the fluid in the inflated balloon protects esophagus 24 from heat generated by transducer 102, by cooling the esophagus. Furthermore, the cooling provided by the fluid protects the esophagus from any collateral damage that may be caused during an ablation procedure in the vicinity of the esophagus, such as an ablation of the posterior wall of the left atrium.

In some embodiments the size of the inflated volume of the balloon may be adjusted by controller 32. Such adjustment allows repositioning of transducer 102 while capsule 22 is in a relatively fixed position in the esophagus. In embodiments where the capsule is asymmetrically located within the inflated balloon, the asymmetry may also be used for the repositioning. This type of repositioning of the transducer may be performed in addition to, or instead of, the repositioning provided by MEMS based pistons 104 and/or MEMS rotation engine 108.

In an unlocking step 208, the operator unlocks the capsule from the applicator tube. To perform the unlocking operation, the operator pushes locking tube 72 in a distal direction to engage protuberances 156, as shown in diagram 152. The unlocking operation detaches the capsule from the applicator tube.

In an applicator removal step 210, the operator withdraws tube 28 from the patient's esophagus, leaving capsule 22 in place in the esophagus.

In a perform procedure step 212, the operator activates transceiver 103 so that transducer 102 begins scanning heart 38. During the scanning process, the MEMS based pistons 104 are activated to scan different segments of the heart. Additionally or alternatively, the MEMS rotation engine 108 is activated to direct the ultrasonic scanning. Further alternatively, the inflation of balloon 92 may be adjusted to alter the position of transducer 102. For example, the inflation may be configured to increase or decrease the distance between the heart and the transducer, so increasing or decreasing the field of view of the transducer.

The activation of the MEMS devices and the balloon inflation may be performed by the operator, semi-automatically by the operator in conjunction with controller 32, or substantially automatically by the controller with overall input from the operator. The MEMS devices allow transducer 102 to be moved from side to side as well as up or down, and inflation or deflation of the balloon typically moves the transducer laterally.

Typical procedures that may be performed by capsule 22 include, but are not limited to:

Automatic imaging of segments of chambers of interest, for example by identifying characteristic anatomical landmarks, as well as verification of the completeness of the chamber images. The identification may be performed using any convenient method of imaging landmarks, for example, by color flow Doppler imaging.

Using one or more electrodes 98 to record esophageal and/or defibrillation signals.

High frame rate electromechanical wave imaging (EWI). By using EWI an electrical activation map of the heart portrayed on the anatomy derived from ultrasound may be generated. Such a map may be generated even before an intra-cardiac catheter probe is introduced into the heart. Generating the map in this way decreases procedure time and obviates the need to acquire a full point-by-point map by touching the endocardial surface of the heart with a catheter.

Continuous tracking and visualization, using screen 44, of an electrophysiological catheter in heart 38. The tracking enables automatic registration of the catheter to capsule 22. The tracking also enables guidance of the catheter during its operation, for example, if it is being used in a trans-septal procedure.

Preplanning and simulation of a future procedure.

Guidance of an ablation procedure, by imaging tissue as it is being ablated.

Assessment of characteristics of a lesion using elastography. The elastography may be performed by transducer 102 directing acoustic radiation force impulses (ARFI) to heart 38, and/or by using EWI.

Real-time detection of complications during performance of a parallel procedure. Complications that may be detected during a parallel ablation procedure include, for example, pericardial effusion, thrombi, and valve damage.

In some embodiments, transducer 102 may be configured to perform guided, non-invasive, high intensity focused ultrasound (HIFU) ablation on tissue of the patient.

Other examples of procedures that may be performed using system 20 are described below.

During the procedure, if the operator considers it necessary, the operator may reintroduce applicator tube 28 into the patient's esophagus, and reattach the tube to capsule 22. Once reattached, the operator may move the capsule to a different location and/or orientation, detach the tube from the capsule, and withdraw the tube from the esophagus, the capsule remaining in its new position.

In a final step 214, after completion of the procedure of step 212, capsule 22 may be withdrawn from the patient via esophagus 24 and the patient's mouth, after deflation of balloon 92. The withdrawal may be accomplished by gently pulling the capsule using cable 34 and/or tubing 76, or by reattaching the applicator tube and using it to withdraw the capsule.

It will be appreciated that embodiments of the present invention significantly improve the comfort level, and reduce the sedation required, for patients during a procedure comprising transesophageal imaging, compared to prior art systems using a thick tube in the esophagus. Such improved comfort level and reduced sedation enables times of procedures using transesophageal imaging to be extended significantly. Furthermore, since transducer 102 may be oriented and positioned by MEMS systems 104, 108 and/or balloon 92, complete imaging of a desired tissue may be achieved over the extended period available for any given procedure.

Consequently, capsule 22 may be advantageously used for real-time, typically 3D, cardiac imaging for diagnosis and/or online guidance of therapeutic procedures. Such procedures include cardiac ablation, pacemaker placement, CRT (cardiac resynchronization therapy) electrode placement, and valve repair. In addition, embodiments of the present invention enable automatic, hands free, closed-loop continuous tracking of a catheter or electrode lead, or another tool. Alternatively or additionally, capsule 22 may be implemented to enable automatic compensation of respiratory motion.

Figure 7:
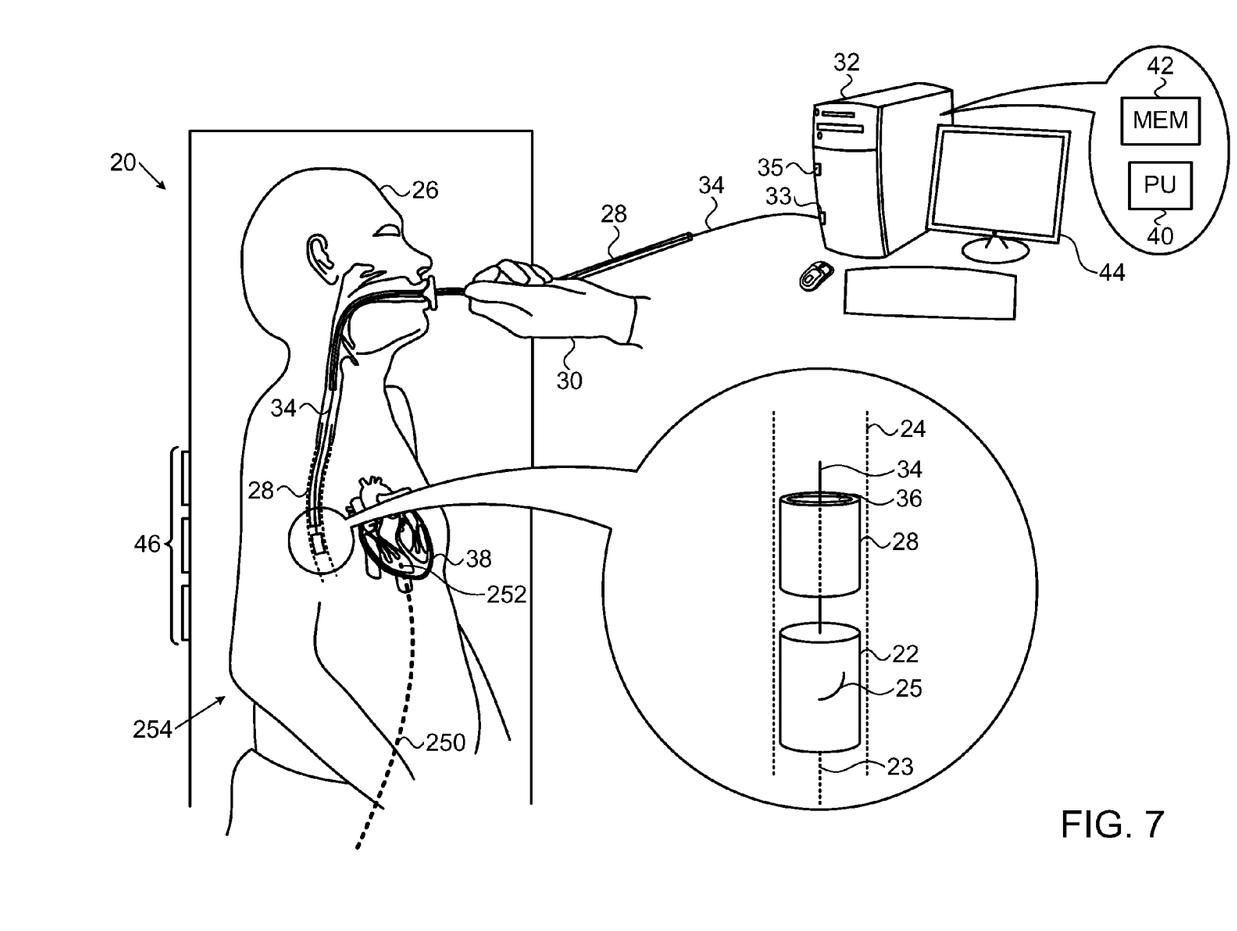
FIG. 7 is a schematic diagram illustrating a procedure using the imaging system, according to an embodiment of the present invention.
Figure 8:
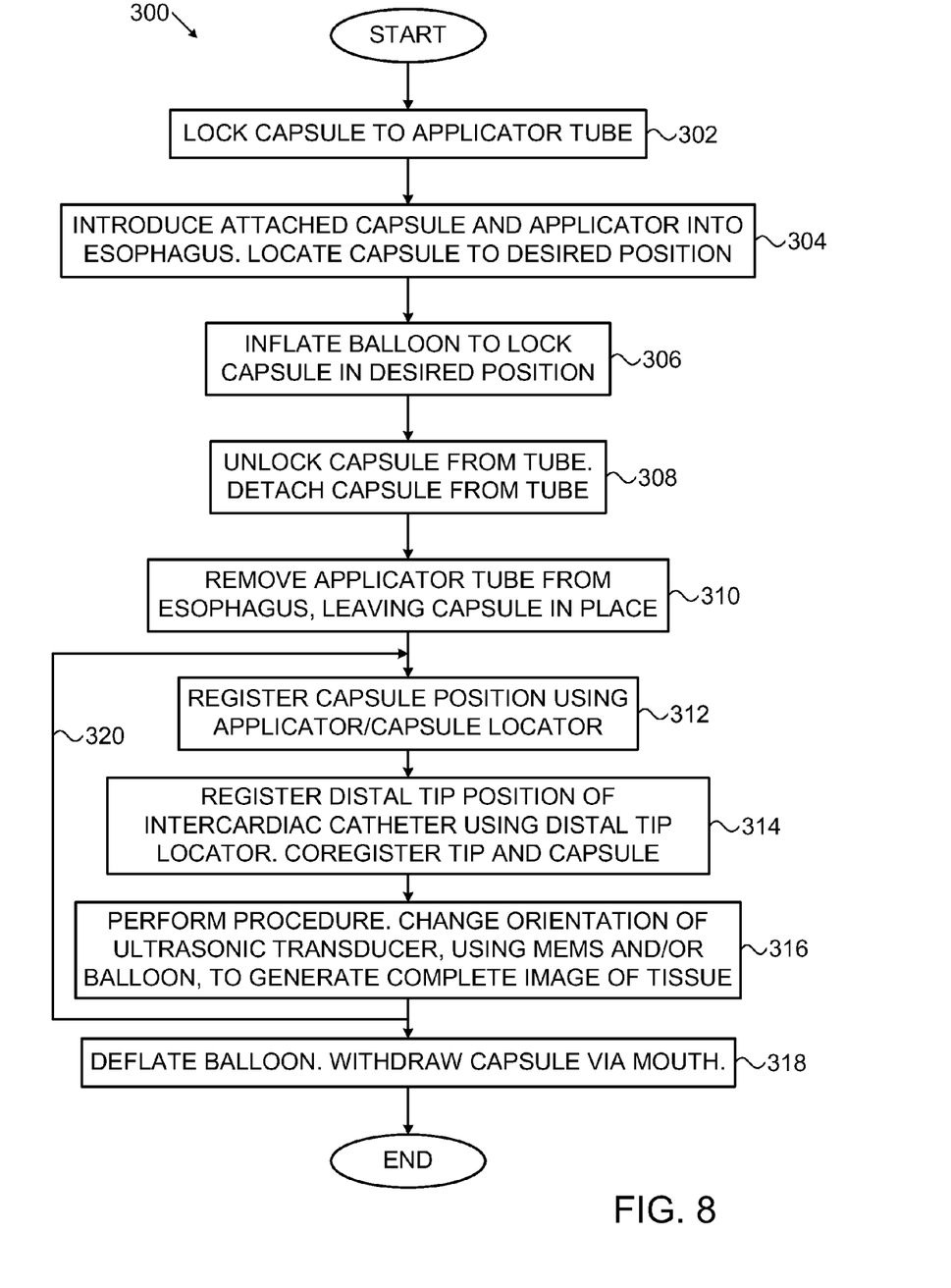
FIG. 8 is a flowchart describing steps of the procedure, according to an embodiment of the present invention.

FIG. 7 is a schematic diagram illustrating a procedure using imaging system 20, and FIG. 8 is a flowchart 300 describing steps of the procedure, according to embodiments of the present invention. In FIG. 7, an intercardiac catheter probe 250 is used in a cardiac procedure, so that a distal tip 252 of the probe enters heart 38. Distal tip 252 is assumed to comprise a tip locating device 254, such as a magnetic locating device used in the CARTO® navigation system referred to above, or alternatively a hybrid magnetic and impedance tracking device such as provided in the CARTO 3® system produced by Biosense Webster, or further alternatively an impedance tracking device. For clarity, in the following description the distal tip is assumed to be tracked using fields generated by magnetic transmitters 46.

For simplicity, the description relates only to tracking the distal tip. Those having ordinary skill in the art will be able to adapt the description to cover other parts of probe 250, such as its shaft, which may have locating devices, as well as to adapt the description when mechanical properties, such as elasticity of the probe, are known.

While the description relates to tracking one probe; it will be understood that more than one probe may be tracked substantially simultaneously, and that the different probes may have different characteristics. For example a first probe may be a linear ablation probe, a second probe may comprise a lasso probe.

In the following description, capsule locator 100 in capsule 22 and applicator distal end locator 66 are assumed to comprise magnetic locating devices that are also tracked using the fields from transmitters 46.

Operations performed in steps 302-310 of flowchart 200 are respectively substantially the same as steps 202-210 of flowchart 200 (FIG. 6).

In a capsule registration step 312, the position of the capsule relative to transmitters 46 is determined using the capsule locator and/or the applicator distal end locator.

In an intercardiac registration step 314, the position of probe distal tip 252 relative to transmitters 46 is determined, using locator 254. The positions of the capsule and the probe distal tip are then registered with each other, for example, by calculating a vector between the two positions. It will be understood that the registration is highly accurate since the two positions are measured using the same magnetic transmitters 46.

A procedure step 316 is substantially the same as step 212 of flowchart 200. During step 316 the intercardiac procedure is performed, so that images of heart 38 and distal tip 252, as well as an accurate relative location of the distal tip, are generated. An arrow 320 indicates that during the procedure steps 312, 314, and 316 may be implemented in an iterative manner, so that the registration of capsule 22 and distal tip 252 with each other is continuously updated in real time.

A final step 318, performed when the procedure of step 316 has completed, is substantially the same as step 214 of flowchart 200.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. An imaging system, comprising:
a capsule, configured to enter an esophagus of a patient, comprising an ultrasonic transducer configured to image tissue of the patient, and one or more microelectronic mechanical systems (MEMs), which are configured to position and reorient the ultrasonic transducer so that ultrasound from the transducer is directed towards the tissue of the patient in multiple positions to generate a scanned image of the tissue, and a balloon which is inflatable with a fluid, and is configured to only partially surround the capsule so that the capsule is located asymmetrically within the balloon, and to fix the capsule to the esophagus when the balloon is in an inflated state, the balloon comprising one or more electrodes for recording defibrillation signals;

an applicator tube having a central cavity and being configured to enter the esophagus, the tube being attachable to the capsule for positioning the capsule within the esophagus, and being detachable from the capsule after positioning of the capsule so as to permit the tube to be withdrawn from the esophagus while the capsule remains in position in the esophagus; and a controller cable attached to the capsule and slideable within the central cavity, the capsule, applicator tube and controller cable being configured such that the controller cable remains attached to the capsule when the applicator tube is detached and withdrawn from the esophagus.

2. The imaging system according to claim 1, wherein the applicator tube comprises a locking mechanism, and wherein the capsule comprises a retaining mechanism which mates with the locking mechanism, the locking mechanism and the retaining mechanism being operable so as to attach the tube to the capsule, and detach the tube from the capsule while the capsule is in the position in the esophagus by deactivation of the locking mechanism outside the esophagus.

3. The imaging system according to claim 1, further comprising a cable traversing a cavity of the applicator tube and coupled to the capsule, the cable being configured to transfer signals to and from the capsule.

4. The imaging system according to claim 3, wherein the signals comprise imaging signals generated by the ultrasonic transducer.

5. The imaging system according to claim 1, further comprising tubing connected to the capsule via a cavity of the applicator tube, the tubing being configured to deliver the fluid to the balloon.

6. The imaging system according to claim 1, wherein a position of the transducer is adjusted in response to the inflation of the balloon.

7. The imaging system according to claim 1, wherein the capsule comprises a capsule locator, configured to provide at least one of a location and an orientation of the capsule.

8. The imaging system according to claim 7, wherein the capsule locator comprises a magnetic locating device.

9. The imaging system according to claim 1, wherein the applicator tube comprises a tube locator, configured to provide at least one of a location and an orientation of a distal end of the applicator tube.

10. The imaging system according to claim 1, wherein the capsule is cylindrical.

11. The imaging system according to claim 10, wherein the cylindrical capsule has a helical characteristic.

12. The imaging system of claim 1 further including a MEMS rotation engine configured to rotate the capsule.

13. A method for imaging, comprising:
Inserting an imaging system into an esophagus of a patient, the imaging system having a capsule, an applicator tube including a central cavity, a controller cable attached to the capsule and slidable within the central cavity, an ultrasonic transducer configured to image tissue of the patient and a balloon which is inflatable with a fluid, and is configured to only partially surround the capsule so that the capsule is located asymmetrically within the balloon, and to fix the capsule to the esophagus when the balloon is in an inflated state, the balloon comprising one or more electrodes for recording defibrillation signals; and inserting the applicator tube into the esophagus, the tube being attachable to the capsule for positioning the capsule within the esophagus, and being detachable from the capsule after positioning of the capsule so as to permit the tube to be withdrawn from the esophagus while the capsule remains in position in the esophagus attached to the controller cable;

positioning and reorienting the ultrasonic transducer using one or more microelectronic mechanical systems (MEMs) so that ultrasound generated by the transducer is directed towards the tissue of the patient in multiple positions to generate a scanned image of the tissue, and recording defibrillation signals with the one or more electrodes.

14. The method according to claim 13, wherein the applicator tube comprises a locking mechanism, and wherein the capsule comprises a retaining mechanism which mates with the locking mechanism, the locking mechanism and the retaining mechanism being operable so as to attach the tube to the capsule and detach the tube from the capsule.

15. The method according to claim 13, further comprising threading a cable through a cavity of the applicator tube and coupling the cable to the capsule, the cable being configured to transfer signals to and from the capsule.

16. The method according to claim 13, wherein a position of the transducer is adjusted in response to the inflation of the balloon.

17. The method according to claim 13, wherein the capsule comprises a capsule locator, configured to provide at least one of a location and an orientation of the capsule.

18. The method according to claim 13, wherein the applicator tube comprises a tube locator, configured to provide at least one of a location and an orientation of a distal end of the applicator tube.

19. The method according to claim 13, further including rotating the capsule using a MEMS rotation engine.

20. An imaging system, comprising:
a capsule, configured to enter an esophagus of a patient, comprising an ultrasonic transducer configured to image tissue of the patient, and one or more microelectronic mechanical systems (MEMs), which are configured to position and reorient the ultrasonic transducer so that ultrasound from the transducer is directed towards the tissue of the patient in multiple positions to generate a scanned image of the tissue, and a balloon which is inflatable with a fluid, and is configured to only partially surround the capsule so that the capsule is located asymmetrically within the balloon, and to fix the capsule to the esophagus when the balloon is in an inflated state, the balloon comprising one or more electrodes for recording defibrillation signals;

a capsule locator, fixedly connected to the capsule, comprising a first magnetic locating device providing a first signal, indicative of a first position of the capsule, in response to a magnetic field generated in a vicinity of the patient;

an applicator tube having a central cavity and being configured to enter the esophagus, the tube being attachable to the capsule for positioning the capsule within the esophagus, and being detachable from the capsule after positioning of the capsule so as to permit the tube to be withdrawn from the esophagus while the capsule remains in position in the esophagus;

a probe comprising a second magnetic locating device providing a second signal, indicative of a second position of the probe in the patient and registered with the first position, in response to the magnetic field; and a controller cable attached to the capsule and slideable within the central cavity, the capsule, applicator and controller cable being configured such that the controller cable remains attached to the capsule when the applicator is detached and withdrawn from the esophagus.

21. A method for imaging, comprising:

inserting an imaging system into an esophagus of a patient, the imaging system comprising a capsule comprising an ultrasonic transducer configured to image tissue of the patient, an applicator tube having a central cavity, a controller cable attached to the capsule and slidable within the central cavity and a balloon which is inflatable with a fluid, and is configured to only partially surround the capsule so that the capsule is located asymmetrically within the balloon, and to fix the capsule to the esophagus when the balloon is in an inflated state, the balloon comprising one or more electrodes for recording defibrillation signals; and fixedly connecting a capsule locator to the capsule, the locator comprising a first magnetic locating device providing a first signal, indicative of a first position of the capsule, in response to a magnetic field generated in a vicinity of the patient;

inserting the applicator tube into the esophagus, the tube being attachable to the capsule for positioning the capsule within the esophagus, and being detachable from the capsule after positioning of the capsule so as to permit the tube to be withdrawn from the esophagus while the capsule remains in position in the esophagus attached to the controller cable;

inserting into the patient a probe comprising a second magnetic locating device providing a second signal, indicative of a second position of the probe in the patient and registered with the first position, in response to the magnetic field;

positioning and reorienting the ultrasonic transducer using one or more microelectronic mechanical systems (MEMs) so that ultrasound generated by the transducer is directed towards the tissue of the patient in multiple positions to generate a scanned image of the tissue; and recording defibrillation signals with the one or more electrodes.

* * * * *